(12) United States Patent
Sakai et al.

(10) Patent No.: US 7,907,276 B2
(45) Date of Patent: Mar. 15, 2011

(54) FILM QUALITY EVALUATION METHOD, APPARATUS THEREFOR, AND PRODUCTION SYSTEM FOR THIN-FILM DEVICE

(75) Inventors: Satoshi Sakai, Yokohama (JP); Yoichiro Tsumura, Hiroshima (JP); Masami Iida, Nagasaki (JP); Kohei Kawazoe, Nagasaki (JP)

(73) Assignee: Mitsubishi Heavy Industries, Ltd. (JP)

( * ) Notice: Subject to any disclaimer, the term of this patent is extended or adjusted under 35 U.S.C. 154(b) by 0 days.

(21) Appl. No.: 12/517,200

(22) PCT Filed: Oct. 31, 2007

(86) PCT No.: PCT/JP2007/071178
§ 371 (c)(1),
(2), (4) Date: Jun. 2, 2009

(87) PCT Pub. No.: WO2008/102484
PCT Pub. Date: Aug. 28, 2008

(65) Prior Publication Data
US 2010/0067010 A1  Mar. 18, 2010

(30) Foreign Application Priority Data
Feb. 20, 2007  (JP) ................ 2007-039596

(51) Int. Cl.
*G01J 3/44* (2006.01)
(52) U.S. Cl. ..................... 356/301; 356/429

(58) Field of Classification Search .... 356/237.1–237.2, 356/429–431, 301, 445, 600
See application file for complete search history.

(56) References Cited

U.S. PATENT DOCUMENTS
2005/0181240 A1*  8/2005  Ishiyama et al. ........... 428/835.2

FOREIGN PATENT DOCUMENTS
| JP | 2001-110864 A | 4/2001 |
|---|---|---|
| JP | 2002-026348 A | 1/2002 |
| JP | 2002-176009 A | 6/2002 |
| JP | 2003-234288 A | 8/2003 |
| JP | 2006-112939 A | 4/2006 |
| JP | 2007-040855 | 2/2007 |
| WO | WO 2006/045621 | 5/2006 |

OTHER PUBLICATIONS

Office Action issued Sep. 16, 2008 from corresponding Japanese Patent Application No. 2007-039596.

* cited by examiner

*Primary Examiner* — Tarifur Chowdhury
*Assistant Examiner* — Tara S. Pajoohi
(74) *Attorney, Agent, or Firm* — Kanesaka Berner & Partners, LLP

(57) ABSTRACT

An object is to improve production efficiency as well as reducing the burden on an operator. Light is radiated on a crystalline silicon film used for a thin-film silicon device, reflection light reflected by the crystalline silicon film is detected, a parameter of the luminance of the detected reflection light is measured, and film quality evaluation of the crystalline silicon film is performed in accordance with whether the parameter of the luminance is within a predetermined proper range or not.

9 Claims, 6 Drawing Sheets

FILM QUALITY EVALUATION METHOD, APPARATUS THEREFOR, AND PRODUCTION SYSTEM FOR THIN-FILM DEVICE

CROSS-REFERENCE TO RELATED APPLICATIONS

The present application is based on International Application No/PCT/JP2007/071178, filed on Oct. 31, 2007, which in turn corresponds to Japanese Application No. 2007-039596 filed on Feb. 20, 2007, and priority is hereby claimed under 35 USC §119 based on these applications. Each of these applications are hereby incorporated by reference in their entirety into the present application.

TECHNICAL FIELD

The present invention relates to a film quality evaluation method for thin films, and more particularly relates to a film quality evaluation method for evaluating film quality of silicon thin films, to a film quality evaluation apparatus, and to a production system for thin-film devices.

BACKGROUND ART

Thin-film silicon devices include thin-film silicon solar cells. In the related art, the use of crystalline silicon films is known in the field of thin-film silicon solar cells. For instance, considering a tandem solar cell as an example, which is one class of multi-junction solar cell in thin-film silicon solar cells, in this tandem solar cell, a layer called a bottom cell is formed between a top cell and a rear surface electrode. The bottom cell has a photoelectric conversion layer with a pin structure, and crystalline silicon is used for the i layer. The crystalline silicon is a thin film in which minute crystals and amorphous regions are present in a mixed state.

Heretofore, one example of a known film quality evaluation method for crystalline silicon is an evaluation method using a Raman peak intensity ratio in a Raman spectroscopic method (for example, see Patent Document 1).

In particular, Raman spectroscopic measurement is performed for crystalline silicon using a Raman spectroscopic analyzer to obtain a ratio ($I_{520}/I_{480}$) of intensity $I_{520}$ of a Raman peak indicating a crystalline state (in the vicinity of a wavelength of 520 $cm^{-1}$) to intensity $I_{480}$ of a Raman peak indicating an amorphous state (in the vicinity of a wavelength of 480 $cm^{-1}$), and the film quality of crystalline silicon is evaluated using this Raman peak intensity ratio ($I_{520}/I_{480}$). The Raman peak intensity ratio can range from 0 to infinity by definition. When the Raman peak intensity ratio is 0, the silicon is considered to be amorphous, and as the Raman peak intensity ratio increases, the degree of crystallinity of a crystalline silicon film is considered to increase.

In the case of crystalline silicon used for a solar cell, a proper range of the Raman peak intensity ratio is determined in accordance with the required quality, and for example, the film quality is evaluated based on whether a measurement value of the Raman peak intensity ratio is within this proper range or not.

Patent Document 1: Japanese Unexamined Patent Application Publication No. 2002-26348

DISCLOSURE OF INVENTION

In the above film quality evaluation using the Raman peak intensity ratio, a Raman spectroscopic measurement apparatus or the like must be used to measure the Raman peak intensity ratio. Hence, when an evaluation inspection is performed, a test piece must be cut out of a substrate removed from a production line, must then be placed in a Raman spectroscopic analyzer which is provided independently of the production line, and must be subsequently evaluated under this condition.

Accordingly, a substrate provided with a thin silicon film which was used for inspection could not be used as a final product, and as a result, the production efficiency was disadvantageously degraded. Another problem is that, since an operator must cut a test piece out of a silicon substrate and then must perform the inspection, a large burden is placed on the operator.

Furthermore, all substrates could not be inspected, and since it took time to obtain an evaluation result, the result could not be fed back to the production line; hence, the production stability was degraded, and consequently, the yield was degraded thereby.

In addition, a method which can easily perform online evaluation of the film quality in a production line has been desired.

The present invention has been conceived to solve the above-described problems, and an object of the present invention is to provide a film quality evaluation method which can improve production efficiency and yield as well as reducing the burden on an operator, a film quality evaluation apparatus, and a production system for thin-film devices.

A first aspect of the present invention is a film quality evaluation method comprising: radiating light on a crystalline silicon film formed on a solar cell substrate from a film surface side; detecting reflection light reflected by the crystalline silicon film; measuring a parameter of the luminance of the detected reflection light; and performing film quality evaluation of the crystalline silicon film in accordance with whether the parameter of the luminance is within a predetermined proper range or not.

The inventors of the present invention newly found phenomena whereby surface irregularities of a crystalline silicon film vary in accordance with the Raman peak intensity ratio, and the scattering behavior of light varies in accordance with the above variation. The inventors of the present invention found that instead of conventional crystallinity evaluation using the Raman peak intensity ratio, the film quality of a silicon thin film, in particular, a crystalline silicon thin film, is evaluated using a parameter of the scattering behavior of light, such as a parameter of the luminance of reflection light.

According to the film quality evaluation method of the present invention, the film quality evaluation of a crystalline silicon film is performed based on whether the parameter of the luminance of reflection light reflected by the surface of a crystalline silicon film formed on a substrate used for a solar cell is within a proper range or not. As described above, since the film quality evaluation of crystalline silicon is performed using the parameter of the luminance of reflection light instead of using the Raman peak intensity ratio, the evaluation inspection can be performed without using a specialized evaluation apparatus, such as a Raman spectroscopic measurement apparatus.

Accordingly, when light is radiated to a production substrate transported in a production line, the film quality evaluation can be performed based on this reflection light, and non-destructive inspection can be performed for all production substrates, so that the yield is improved. Hence, a test piece cut out of a substrate which is removed from the production line is not required, and as a result, the burden on an operator can be reduced.

In the above film quality evaluation method, film quality evaluation of the crystalline silicon may be performed such that parameters of luminances of samples having different Raman peak intensity ratios are respectively detected, a luminance characteristic in which the detected parameters of the luminances are related to the Raman peak intensity ratios is formed, a proper range of the luminance corresponding to a predetermined proper range of the Raman peak intensity ratio is specified in the above luminance characteristic, and the evaluation is performed using the specified proper range of the parameter of the luminance.

According to the method as described above, samples having Raman peak intensity ratios which are known in advance are prepared and irradiated with light to measure parameters of luminances corresponding to the respective Raman peak intensity ratios, and based on the measurement result, a luminance characteristic is formed in which the Raman peak intensity ratio and the parameter of the luminance are related to each other. In addition, values of parameters of luminances corresponding to a predetermined proper range of the Raman peak intensity ratio is obtained to specify a proper range of the parameter of the luminance, and film quality evaluation of crystalline silicon is performed using this proper range.

Accordingly, since the film quality evaluation of crystalline silicon can be performed using a range equivalent to the proper range of the Raman peak intensity ratio which has been conventionally used, the standard of the film quality evaluation can be maintained.

As the parameter of the luminance, for example, color difference or reflectance may be used. In addition, as the color difference, for example, the L* value of the L*a*b* color coordinate system may be used.

In addition, when the reflectance is used as the parameter of the luminance, a reflectance corresponding to an arbitrary wavelength in a wavelength band from the visible range (380 to 760 nm) to the near infrared range (760 nm to 2.5 μm) may be used. A reflectance corresponding to an arbitrary wavelength in the visible range (380 to 760 nm) is preferably used, or a reflectance corresponding to a wavelength of 650 nm or more is more preferably used.

In addition, it was found that when the reflectance is used as the parameter of the luminance, and when crystalline silicon is amorphized, a significant difference is obtained in a wavelength band of 650 nm or more. Hence, when reflectances are compared to each other particularly in a wavelength band of 650 nm or more, the accuracy of film quality evaluation can be improved. The reason the significant difference is observed in a wavelength band of 650 nm or more is the difference in absorption spectra between amorphous silicon and crystalline silicon.

According to the method as described above, since the color difference or reflectance corresponding to an assigned wavelength is used as the reflection light to be evaluated instead of simply measuring reflection light intensity, the influence of the surface condition of a film to be measured is detected, and hence the film quality can be measured with high accuracy.

A second aspect of the present invention is a film quality evaluation apparatus comprising: a light radiation unit radiating light on a crystalline silicon film formed on a substrate from a film surface side; a light detection unit detecting reflection light reflected by the crystalline silicon film; a parameter measurement unit measuring a parameter of the luminance of the detected reflection light; and an evaluation unit performing film quality evaluation of the crystalline silicon film in accordance with whether the parameter of the luminance is within a predetermined proper range or not.

According to the structure as described above, light is radiated to the crystalline silicon film formed on the substrate by the light radiation unit, and this reflection light is detected by the light detection unit. Since the detected light is analyzed by the parameter measurement unit, the parameter of the luminance is measured, and film quality evaluation is performed by the evaluation unit based on whether the measurement result is within a predetermined proper range. As described above, according to the present invention, since the film quality evaluation of a crystalline silicon film is performed based on the parameter of the luminance, the evaluation inspection can be performed without using a specialized evaluation apparatus such as a Raman spectroscopic measurement apparatus.

Accordingly, when light is radiated to a production substrate transported in a production line, the film quality evaluation can be performed based on this reflection light, and non-destructive inspection can be performed for all production substrates, thereby improving the yield. Hence, a test piece cut out from a substrate which is removed from the production line is not required, and as a result, the burden on an operator can be reduced.

In the film quality evaluation apparatus described above, film quality evaluation of the crystalline silicon may be performed such that the evaluation unit detects respective parameters of luminances of samples having different Raman peak intensity ratios to form a luminance characteristic in which the detected parameters of luminances and the Raman peak intensity ratios are related to each other, a proper range of the parameter of the luminance corresponding to a predetermined proper range of the Raman peak intensity ratio is specified in the luminance characteristic, and the film quality evaluation of the crystalline silicon is performed using the specified proper range of the parameter of the luminance.

According to the structure as described above, after samples having Raman peak intensity ratios known in advance are prepared and are irradiated with light, parameters of luminances corresponding to the respective Raman peak intensity ratios are measured, and based on this measurement result, a luminance characteristic in which the Raman peak intensity ratio and the parameter of the luminance are related to each other is formed. In addition, in this luminance characteristic, the values of parameters of the luminance corresponding to a predetermined proper range of the Raman peak intensity ratio are obtained so as to specify a proper range of the parameter of the luminance, and the film quality evaluation of crystalline silicon is performed using this proper range.

Accordingly, since the film quality evaluation of crystalline silicon can be performed using the range equivalent to the proper range of the Raman peak intensity ratio which has been conventionally used, the standard of the film quality evaluation can be maintained.

As the parameter of the luminance, for example, color difference or reflectance may be used. In addition, as the color difference, for example, the L* value of the L*a*b* color coordinate system may be used.

In addition, when the reflectance is used as the parameter of the luminance, a reflectance at a wavelength of 650 nm or more may be used.

It was found that when the reflectance is used as the parameter of the luminance, and when crystalline silicon is amorphized, a significant difference is obtained in a wavelength band of 650 nm or more. Hence, when reflectances are compared to each other, particularly, in a wavelength band of 650 nm or more, the accuracy of film quality evaluation can be improved.

A third aspect of the present invention is a production system for a thin-film device comprising the above-described film quality evaluation apparatus, and in this production system, the light radiation unit is disposed to radiate light from a film surface side on a crystalline silicon film which is formed on a substrate transported in a production line including a thin-film formation process so as to monitor a thin-film formation status. This production system for a thin-film device is preferably used, for example, to monitor the thin-film formation status of a thin-film silicon device.

A fourth aspect of the present invention is a thin-film silicon device produced by using the above-described film quality evaluation apparatus.

In addition, the various aspects described above may be used in combination whenever applicable.

One example of the thin-film silicon device is a thin-film silicon solar cell. In addition, in the thin-film solar cell, in terms of an improvement in power generation efficiency, it is important to form a thin film more uniformly and homogeneously on a large substrate having a side length of 1 m or more, and the film quality of the entire substrate surface can be evaluated using the above film quality evaluation apparatus; hence, the power generation efficiency, yield, and production efficiency are significantly improved.

In the present invention, silicon is a collective term including silicon (Si), silicon carbide (SiC), and silicon germanium (SiGe), and crystalline silicon indicates silicon other than amorphous silicon, that is, silicon other than noncrystalline silicon, and includes crystalline and polycrystalline silicon. In addition, thin-film silicon includes amorphous silicon, crystalline silicon, and multijunction-type silicon (tandem or triple type) in which amorphous silicon and crystalline silicon are laminated to each other.

The present invention is effective in improving the production efficiency as well as reducing the burden on an operator. In addition, since the variation in film quality can be monitored, the present invention is effective in improving the power generation efficiency, yield, and production efficiency.

EXPLANATION OF REFERENCE SIGNS

Figure 1:
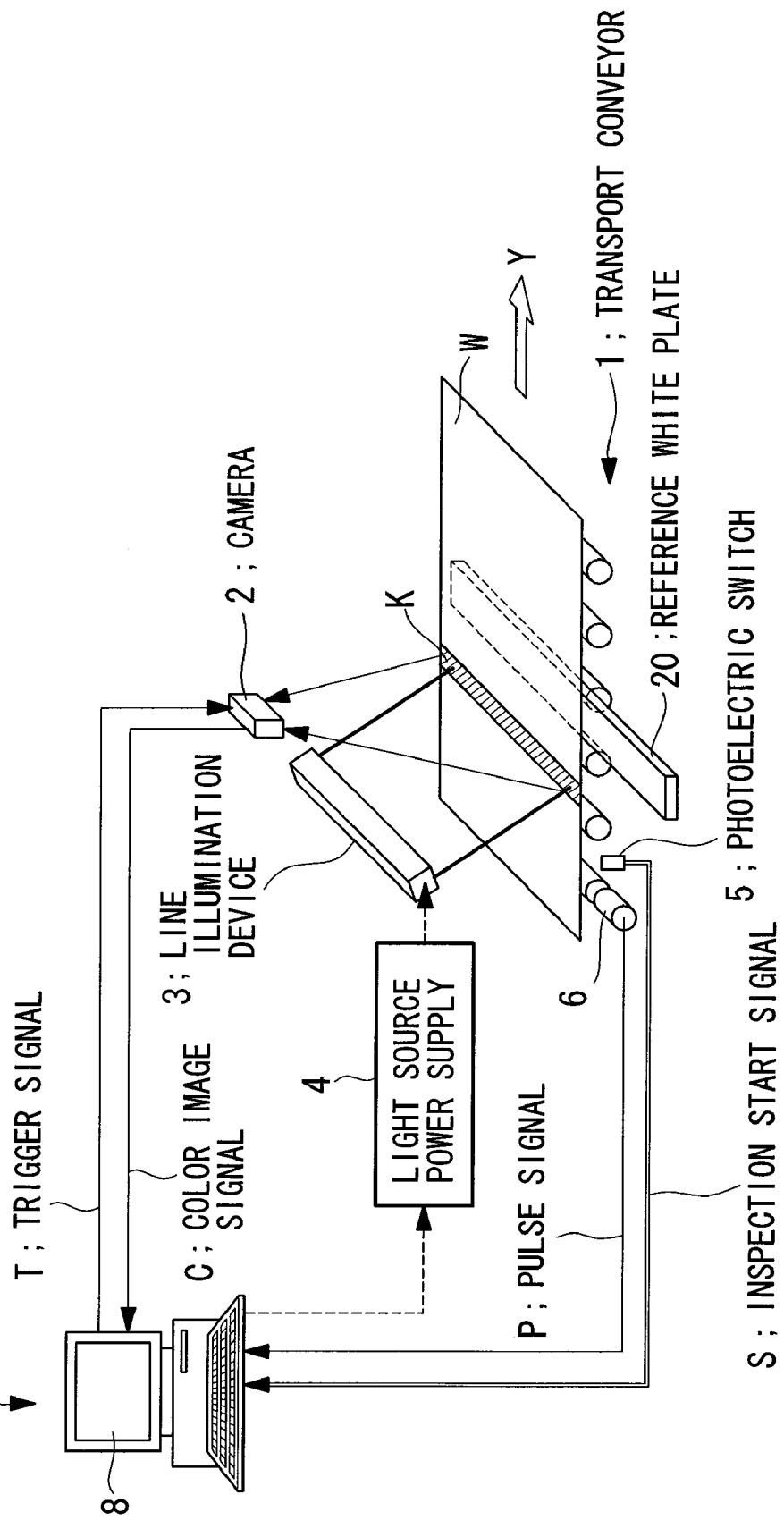
FIG. 1 is a view showing the entire structure of a film quality evaluation apparatus according to a first embodiment of the present invention.

1: transport conveyor
2: camera
3: line illumination device
4: light source power supply
5: photoelectric switch
6: rotary encoder
7: computer
8: display device
W: substrate

BEST MODE FOR CARRYING OUT THE INVENTION

Hereinafter, a film quality evaluation method, an apparatus therefor, and a production system for a thin-film device according to embodiments of the present invention will be described with reference to the accompanying drawings. The film quality evaluation apparatus according to each embodiment is provided for use in part of a production process of a production apparatus for a thin-film silicon device, in particular, a thin-film silicon solar cell.

The film quality evaluation apparatus according to each embodiment is preferably used for performing film quality measurement of a thin film, in particular, a crystalline silicon film, formed on a solar cell substrate. In addition, the film quality evaluation apparatus according to each embodiment can be widely applied to a production system for producing a solar cell having a crystalline silicon layer regardless of the solar cell structure, such as a single solar cell having one pin-structure photoelectric conversion layer, a tandem solar cell having two pin-structure photoelectric conversion layers, a triple solar cell having three pin-structure photoelectric conversion layers, or a monolayer crystalline silicon single film provided on a light transmissive substrate.

According to the present invention, the evaluation of a bottom cell formed between a rear surface electrode and a top cell, that is, the evaluation of a crystalline silicon layer, performed in a production process for a tandem solar cell will be described by way of example.

First Embodiment

FIG. 1 is a view showing the entire structure of a film quality evaluation apparatus according to the first embodiment of the present invention.

In FIG. 1, a transport conveyor 1 transports a substrate W on which a crystalline silicon layer to be inspected is formed in a transport direction (Y direction in the figure). This substrate W is composed, for example, of a transparent conductive film formed by a thermal CVD apparatus, an amorphous silicon film photoelectric conversion layer formed by a plasma CVD apparatus, and a crystalline silicon film photoelectric conversion layer formed by a plasma CVD apparatus, provided in that order on a transparent glass substrate. Alternatively, this substrate W may be composed of a transparent conductive film formed by a thermal CVD apparatus and a crystalline silicon film photoelectric conversion layer formed by a plasma CVD apparatus, provided in that order on a transparent glass substrate.

Alternatively, this substrate W may be composed of a microcrystalline silicon film formed by a plasma CVD apparatus on a transparent glass substrate. In FIG. 1, the transparent glass substrate is located at the transport conveyor 1 side of the substrate W, and the transparent conductive film and the thin-film silicon photoelectric conversion layer laminated thereto are located at the side opposite to the transport conveyor 1. A camera (light detection unit) 2 and a line illumination device (light radiation unit) 3 are provided above the transport conveyor 1.

As the camera 2, for example, a color line sensor camera, a color area camera, or a so-called CCD camera may be used. In this embodiment, as the camera 2, a camera formed of an image pickup element (such as a CCD element) and an image pickup lens system is used.

The line illumination device 3 is composed, for example, of a fluorescent lamp, and when a light source power supply 4 is operated based on a signal sent from a computer 7, which will be described later, adjustment of light intensity and ON/OFF control of a light source are performed. The line illumination device 3 is not limited to a fluorescent lamp, so long as it is a light source that can radiate white light in the form of a line; line LED illumination formed by arranging LED devices in a straight line may be used.

Figure 2:
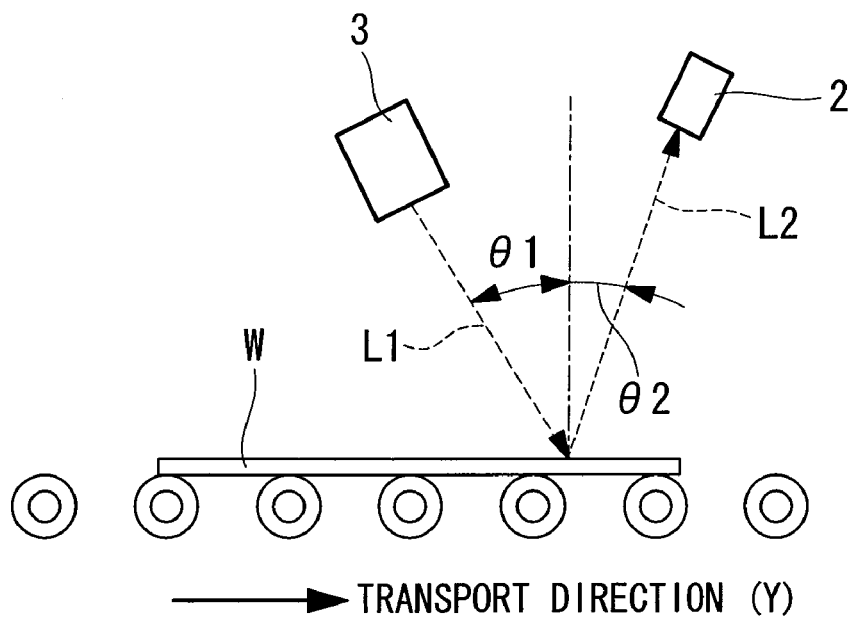
FIG. 2 is a view showing the arrangement of a camera and a line illumination device.

The camera 2 and the line illumination device 3 are disposed as shown in FIG. 2 to form a reflection-type inspection device which faces a film surface to be measured. That is, the line illumination device 3 is disposed so that line illumination light L1 radiated therefrom is reflected at an upper surface of the substrate W, that is, in this embodiment, is reflected at a surface of a crystalline silicon film formed on the surface of the substrate W.

The camera 2 is disposed at a position on which line reflection light L2 reflected by the surface of the crystalline silicon film is incident so as to receive the reflection light L2 reflected by a portion (line portion K in FIG. 1) on which the line illumination light L1 is incident. The camera 2 and the line illumination device 3 are disposed so that an incident angle θ1 of the line illumination light L1 incident on the substrate W is approximately 45° and a reflection angle θ2 of the line reflection light L2 reflected by the substrate W is approximately 0°.

In a film thickness measurement apparatus according to this embodiment, the incident angle θ1 may be any angle from approximately 0° to 90°, and the reflection angle θ2 may be in the vicinity of 0°. By the arrangement described above, the adjustment of a camera position, that is, focusing, can be easily performed.

A photoelectric switch 5 and a rotary encoder 6 are disposed at the transport conveyor 1. When the photoelectric switch 5 detects that a front end portion of the substrate W thus transported has reached the incident position of the line illumination light L1, that is, at line image acquisition position to be acquired by the camera 2, it generates an inspection start signal S and sends it to the computer 7. The rotary encoder 6 generates a pulse signal P and sends it to the computer 7 each time it rotates by a prescribed angle, that is, each time the substrate W is transported a predetermined distance.

In addition, a reference white plate 20 is provided under the transport conveyor 1 at a position to which the line illumination light L1 is radiated. This reference white plate 20 is used to obtain luminance information used as a reference. The material for the reference white plate 20 is not particularly limited, and any material having high uniformity which can be regarded as a reference in the field of image capturing may be used.

In this embodiment, the white color is mentioned for the sake of convenience; however, strict white in terms of chromatics is not always required, and a unique color may also be used. For example, it is possible to use a white plate (made by consolidating aluminum sulfate powder into pellets) generally used in spectroscopy, paper, a white reference generally used in commercially available colorimeters, or a material having high uniformity that can be regarded as a reference.

After receiving the inspection start signal S, the computer 7 is designed to send a trigger signal T to the camera 2 each time it receives the pulse signal P. Each time the camera 2 receives the trigger signal T, the camera 2 captures an image of the substrate W, receives the reflection light radiated from the line illumination device 3, generates a color image signal C including image information of one line which has a width equal to that of the substrate W and a length in the transport direction, and sends this color image signal C to the computer 7. This color image signal C includes, for example, a red component image signal R, a green component image signal G, and a blue component image signal B.

When receiving a plurality of color image signals C from the camera 2, the computer (parameter measurement unit and evaluation unit) 7 arranges these color signals C in a two-dimensional manner in a memory, so that a two-dimensional image showing a surface image of the substrate W and the film quality distribution are formed.

The computer 7 performs a film quality evaluation process on the two-dimensional image thus formed, so that the film quality evaluation of the crystalline silicon film formed on the substrate W is carried out. In addition, a display device 8 such as a CRT is connected to the computer 7, and the waveform of the color image signal C, an image-processed two-dimensional image, the evaluation results, and the like are displayed on this display device 8.

Next, the case in which the substrate W, which is an inspection object, is actually inspected by the film quality evaluation apparatus shown in FIG. 1 will be described.

First, while the line illumination device 3 is turned on, the computer 7 transports the substrate W placed on the transport conveyor 1 in a transport direction. Accordingly, the line illumination light L1 (see FIG. 2) radiated from the line illumination device 3 is reflected by the crystalline silicon film formed on the substrate W. In addition, the pulse signal P is sent to the computer 7 from the rotary encoder 6 in accordance with the movement of the substrate W. The computer 7 sends the trigger signal T to the camera 2 each time it receives this pulse signal P.

Consequently, the line reflection light L2 (see FIG. 2) is received by the camera 2 as the substrate W is moved, so that the color image signals C are sequentially sent to the computer 7. When the computer 7 receives many lines of the color image signals C supplied from the camera 2, these signals are two-dimensionally arranged to form a two-dimensional image.

When the two-dimensional image is formed as described above, the computer 7 carries out the following film quality evaluation process, so that the film quality evaluation is performed. Hereinafter, the film quality evaluation process will be described in detail.

First, in the computer 7, image processing is performed on the two-dimensional image to measure parameters of the luminance. When the film quality is evaluated, instead of simply using the reflection light intensity, the relationship between the film quality and the luminance is found, and this relationship is used. In this embodiment, for example, the RGB image data is converted into the CIE-XYZ color coordinate system (Step SA1 in FIG. 3). This conversion can be performed using a known technique.

Next, the CIE-XYZ color coordinate system is converted into the CIE-L*a*b* color coordinate system (Step SA2). L*a*b* is the L*a*b* (L-star, a-star, b-star) color coordinate system in accordance with JIS Z8729 and represents the color difference. L*, a*, and b* represent the brightness (luminance), the chromaticness index of a red-to-green hue, and the chromaticness index of a yellow-to-blue hue, respectively.

When the L* value (luminance) of the two-dimensional image is obtained as described above, the computer 7 determines whether the L* value of each pixel obtained by the camera 2 is in a predetermined proper range or not, and the entire two-dimensional image is categorized into a proper region and an improper region (Step SA3). Hence, the substrate W can be divided into the proper region and the improper region.

Next, the ratio of the area of the proper region to the total area of the substrate is obtained (Step SA4), and it is determined whether this ratio is a predetermined standard value or more (Step SA5). When this value is the standard value or more, the quality is judged good (Step SA6), and when this value is less than the standard value, the quality is judged defective (Step SA7).

Figure 3:
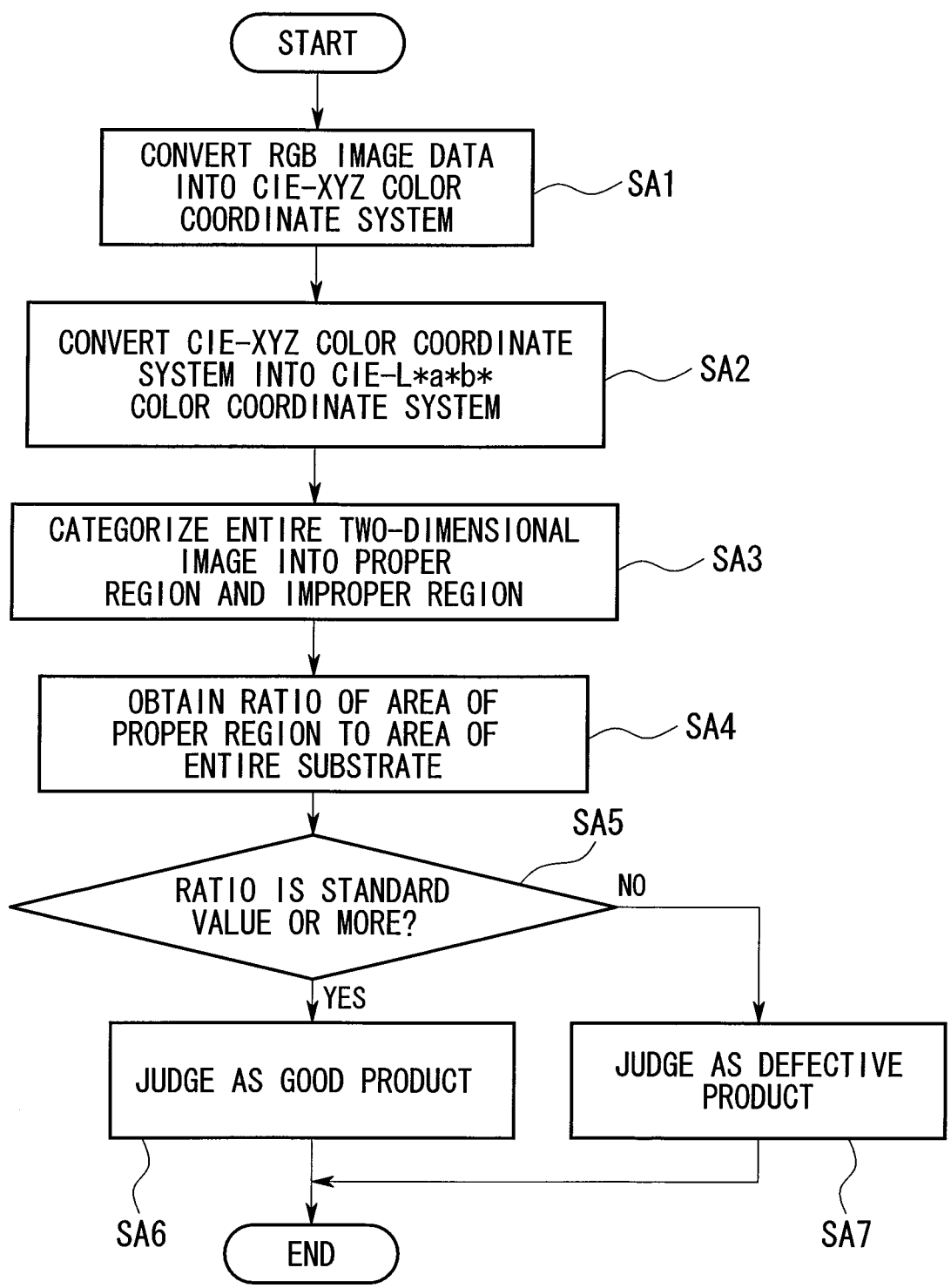
FIG. 3 is a flowchart showing a procedure of a film quality evaluation process carried out by the film quality evaluation apparatus according to the first embodiment of the present invention.

Each time the two-dimensional image is formed based on the color image signals sent from the camera 2, the computer 7 repeatedly performs the thin-film evaluation process shown in FIG. 3, so that the film quality evaluation of each substrate is carried out.

Figure 4:
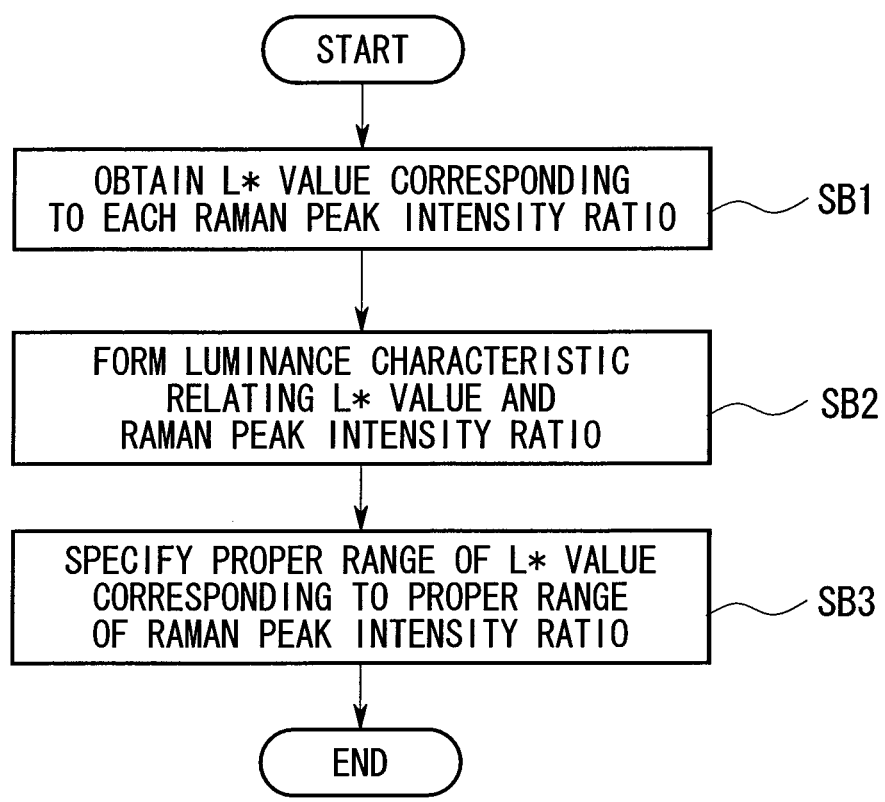
FIG. 4 is a flowchart showing a procedure for determining an application range used in the film quality evaluation process of the present invention.

Next, a method for setting a proper range that is referred in the Step SA3 will be described with reference to FIG. 4.

First, samples formed of a material approximately similar to that of a film to be evaluated and having a similar thickness thereto are prepared, the samples having different Raman peak intensity ratios which are known in advance by separately performing measurement and evaluation using a Raman spectroscopic analyzer or the like. The samples are each placed on a transport line 1 shown in FIG. 1, the line illumination device 3 radiates the illumination light, the camera 2 receives the reflection light, and the computer 7 performs image layer processing. The L* value of each sample is obtained by the above method (Step SB1 in FIG. 4).

Figure 5:
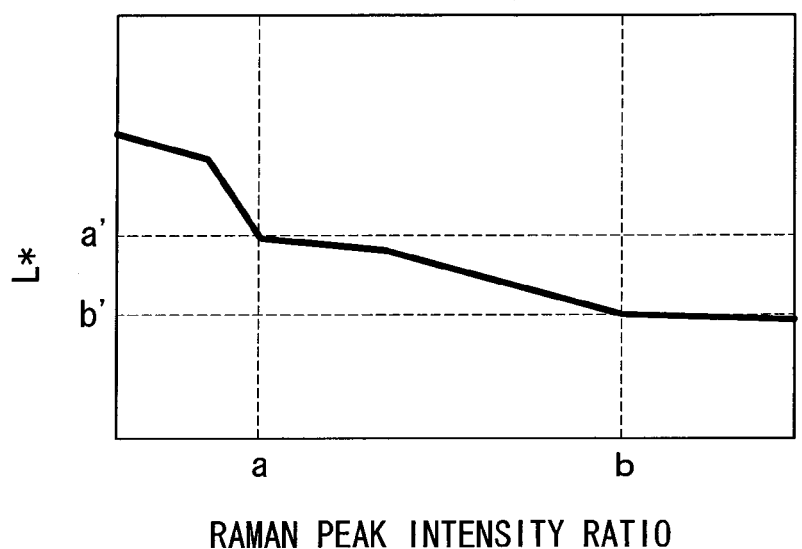
FIG. 5 is a view showing one example of a luminance characteristic formed in the process shown in FIG. 4.

Accordingly, L* values corresponding to the different Raman peak intensity ratios can be obtained. Subsequently, a luminance characteristic relating the obtained L* values to the Raman peak intensity ratios is formed (Step SB2). In this step, coordinate axes in which the horizontal axis indicates the Raman peak intensity ratio and the vertical axis indicates the L* value are formed, and the experimental results are plotted on the axes to form the luminance characteristic. For example, the luminance characteristic is shown in FIG. 5 by way of example.

Since the evaluation of the film quality is performed using the film surface condition, the direct influence of irregularities of an underlying layer, such as a transparent conductive film of a solar cell, is small. However, the crystalline film is influenced by variations in crystal growth caused by an underlying layer or by the crystal growth as the film thickness is increased, and as a result, the surface condition of the film may vary. Hence, when the luminance characteristic as shown in FIG. 5 is formed based on the sample film quality, the underlying layer and the film thickness of the sample are more preferably equal to those to be actually evaluated.

Next, in this luminance characteristic, the proper range of the L* value corresponding to the proper range of the Raman peak intensity ratio which has been conventionally used is specified (Step SB3), whereupon this process is completed. For example, when the proper range of the Raman peak intensity ratio which has been conventionally used is in the range from a value b to a value a shown in FIG. 5, an a' value of L* corresponding to the value a and a b' value of L* corresponding to the value b are obtained, so that the proper range of the L* value is specified in the range from a' to b'.

When the evaluation process described above is performed, the regions described above can be categorized based on whether the L* value is within this proper range from a' to b' or not. In this embodiment, the case in which all the steps are automatically performed by the computer 7 is described; however, the specification of this proper range may be performed by a technician. That is, the method of obtaining a proper range is not particularly limited so long as the proper range of the L* value obtained by the method described above is registered in the computer 7 in the film quality evaluation.

As has thus been described, according to the film quality evaluation apparatus of this embodiment, since the film quality evaluation of crystalline silicon is performed using the L* value instead of using the Raman peak intensity ratio, the film quality evaluation can be performed without using a specialized apparatus such as a Raman spectroscopic measurement apparatus. The reason for this is that the relationship between the L* value of the CIE-L*a*b* color coordinate system and the Raman peak intensity ratio for evaluating the crystalline state is found because of the discovery of phenomena whereby the surface shape of a crystalline silicon film to be evaluated varies in accordance with the Raman peak intensity ratio, and the scattering behavior of light varies in accordance with this variation in shape.

Hence, when the line illumination light L1 is radiated to the substrate W which is transported in the production line, the above film quality evaluation can be performed based on this line reflection light L2; hence, it is not necessary to obtain a test piece by cutting a substrate which is removed from the production line, and as a result, the burden on an operator can be reduced. In addition, since all crystalline silicon films formed by a plasma CVD apparatus can be judged as to whether the quality is good or bad based on the measurement results of this film quality distribution, when defects are detected, the defective films can be taken out during the process, and whenever necessary, for example, film formation conditions of a plasma CVD apparatus can be adjusted.

In addition, when film formation is defective due to a problem that cannot be detected by the plasma CVD apparatus itself, such a situation can be identified immediately and corrective measures quickly taken. That is, by performing evaluation using the average film thickness, which is the item to be controlled, and the standard value of film quality distribution, and by monitoring the film-formation status on-line, production conditions giving high electricity generating efficiency can be maintained, and the occurrence of defects can be identified within a very short period of time; hence the quality of the film formation is stabilized and the yield thereof is improved. Accordingly, the production efficiency is improved.

Furthermore, according to the film quality evaluation apparatus of this embodiment, after L* values corresponding to the predetermined proper range of the Raman peak intensity ratio are obtained, the proper range of the L* values is specified, and the film quality evaluation of crystalline silicon is performed using this proper range; hence, the film quality evaluation of crystalline silicon can be performed using a range equivalent to the proper range of the Raman peak intensity ratio which has been conventionally used. Hence, the standard of the film quality evaluation can be maintained.

In the embodiment described above, the L* value is used as the parameter of the luminance; however, the parameter of the luminance is not limited thereto. For example, instead of the L* value, the reflectance or the light intensity of the line reflection light L2 may also be used.

When the reflectance is used as the parameter of the luminance, the computer 7 detects the reflectance based on the color image signal. As a method for measuring the reflectance, a known method may be appropriately used. In addition, depending on whether the reflectance measured as described above is within a predetermined proper range or not, the two-dimensional image is categorized into a proper region and an improper region, and the substrate is then judged good or bad in accordance with the ratio of the proper region to the total area.

When the reflectance is used as the parameter of the luminance as described above, regarding the method for determining the predetermined range, the range may also be specified by a method similar to that for the L* value described above. One example of a luminance characteristic in which the reflectance is used as the parameter of the luminance is shown in FIG. 6.

As described above, a reflectance range from c' to d' corresponding to the range of the Raman peak intensity ratio from a to b is obtained, and this range may be used for actual film quality evaluation as a proper range of the reflectance.

Figure 7:
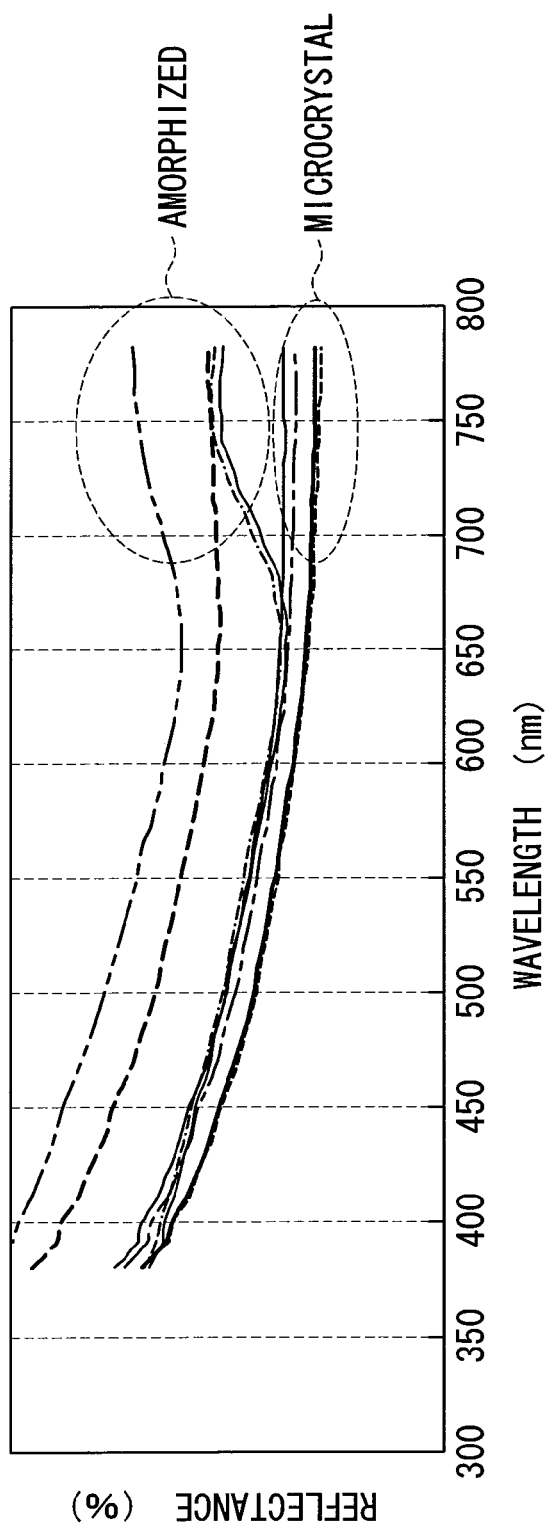
FIG. 7 is a view showing spectral reflection spectra of crystalline silicon and amorphized silicon.

In addition, when the reflectance is used as the parameter of the luminance, it was confirmed by experiments, as shown in FIG. 7, that in a region of a reflection spectrum in which the wavelength is 650 nm or more, the reflectance of an amorphized material is significantly different from that of a non-amorphized material. Hence, when the proper range is determined by using the reflectance in a wavelength band in which the difference is clearly observed, as described above, the evaluation accuracy of the amorphization can be improved.

Figure 6:
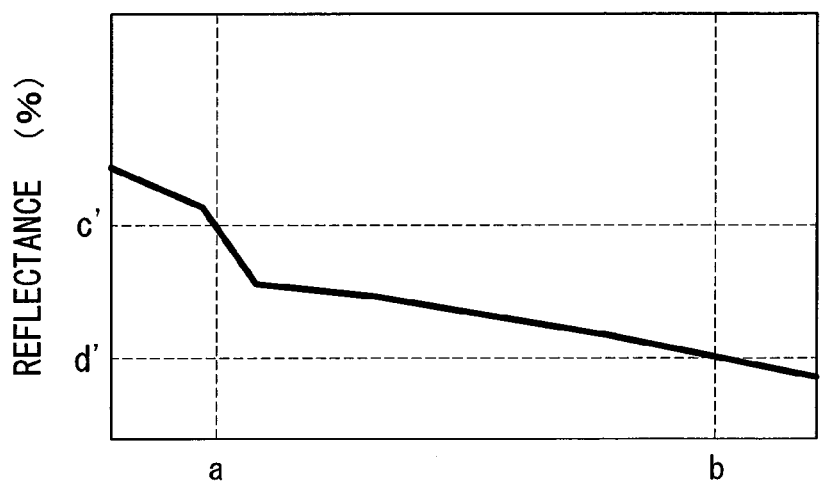
FIG. 6 is a view showing one example of a luminance characteristic in the case in which the reflectance is used instead of the L* value.

In the above embodiment, the proper range of the parameter of the luminance which corresponds to the proper range of the Raman peak intensity ratio is obtained in advance, and the evaluation is performed by using the proper range described above; however, instead of the above method, after Raman peak intensity ratios which have the luminance characteristic as shown in FIG. 5 or 6 and which correspond to respective L* values or reflectances obtained from a two-dimensional image are obtained from the luminance characteristic shown in FIG. 5 or 6, and the film quality evaluation may be performed based on whether an obtained Raman peak intensity ratio is within a predetermined proper range or not. By the method as described above, the film quality evaluation can be performed based on a similar judgmental standard.

In addition, in the above embodiment, although the case in which the film quality of a crystalline silicon film of a tandem solar cell is evaluated is described, the film quality evaluation apparatus of the present invention may also be widely applied to film quality evaluation of a crystalline silicon film used for a thin-film silicon device and a thin-film solar cell.

Second Embodiment

Next, a film quality evaluation apparatus according to the second embodiment of the present invention will be described. Although the film quality evaluation apparatus according to this embodiment is approximately equivalent to that of the above first embodiment, the arrangement of the camera 2 and the line illumination device 3 is different.

Hereinafter, points different from those of the film quality evaluation apparatus according to the first embodiment will be primarily described.

In the film quality evaluation apparatus according to this embodiment shown in FIG. 2, for example, the arrangement of the camera 2 and the line illumination device 3 is set such that the incident angle θ1 of the line illumination light L1 incident on the substrate W is in the vicinity of 0°, and that the reflection angle θ2 of the line reflection light L2 reflected by the substrate W is an angle from approximately 0° to approximately 90°. For example, the arrangement of the camera 2 and the line illumination device 3 is set such that the incident angle θ1 of the line illumination light L1 incident on the substrate W is approximately 0°, and that the reflection angle θ2 of the line reflection light L2 reflected by the substrate W is approximately 45°.

With the arrangement described above, the position adjustment of the line illumination device, that is, the adjustment of the illuminance distribution, can be easily performed.

Third Embodiment

Next, a film quality evaluation apparatus according to the third embodiment of the present invention will be described. Although the film quality evaluation apparatus according to this embodiment is approximately equivalent to that of the above first embodiment, the arrangement of the camera 2 and the line illumination device 3 is different.

Hereinafter, points different from those of the film quality evaluation apparatus according to the first embodiment will be primarily described.

In the film quality evaluation apparatus according to this embodiment shown in FIG. 2, for example, the arrangement of the camera 2 and the line illumination device 3 is set such that the incident angle θ1 of the line illumination light L1 incident on the substrate W is approximately equivalent to the reflection angle θ2 of the line reflection light L2 reflected by the substrate W. For example, the incident angle θ1 of the line illumination light L1 is set to be an angle in the range from approximately 0° to approximately 90°. As one example, the incident angle θ1 and the reflection angle θ2 are set to be an angle from approximately 17° to approximately 18°.

With the arrangement described above, since the specular reflection light can be received, the light receiving level is increased, and it is possible to increase the resistance against disturbances, such as stray light.

The invention claimed is:

1. A film quality evaluation method comprising:
   radiating light on a crystalline silicon film formed on a substrate from a film surface side;
   detecting reflection light reflected by the crystalline silicon film;
   measuring a parameter of the luminance of the detected reflection light; and
   performing film quality evaluation of the crystalline silicon film in accordance with whether the parameter of the luminance is within a specified range or not;
   wherein
   parameters of luminances of samples having different Raman peak intensity ratios are detected to form a luminance characteristic in which the detected parameters of luminances and the Raman peak intensity ratios are related to each other, and
   a range of the luminance corresponding to a specified range of the Raman peak intensity ratio is specified in the luminance characteristic, and film quality evaluation of the crystalline silicon is performed using the specified range of the parameter of the luminance.

2. The film quality evaluation method according to claim 1, wherein color difference or reflectance is used as the parameter of the luminance.

3. The film quality evaluation method according to claim 1, wherein a reflectance at a wavelength of 650 nm or more is used.

4. A film quality evaluation apparatus comprising:
   a light radiation unit radiating light on a crystalline silicon film formed on a substrate from a film surface side;
   a light detection unit detecting reflection light reflected by the crystalline silicon film;
   a parameter measurement unit measuring a parameter of the luminance of the detected reflection light; and an evaluation unit performing film quality evaluation of the crystalline silicon film in accordance with whether the parameter of the luminance is within a specified range or not;

wherein the evaluation unit detects parameters of luminances of samples having different Raman peak intensity ratios to form a luminance characteristic in which the detected parameters of luminances and the Raman peak intensity ratios are related to each other, and a range of parameters of luminances corresponding to a specified range of the Raman peak intensity ratio is specified, and film quality evaluation of the crystalline silicon is performed using the specified range of the parameter of the luminance.

5. The film quality evaluation apparatus according to claim 4, wherein color difference or reflectance is used as the parameter of the luminance.

6. A production system for a thin-film device comprising: the film quality evaluation apparatus according to claim 5, wherein the light radiation unit is disposed to radiate light from a film surface side on a crystalline silicon film which is formed on a substrate transported in a production line including a thin-film formation process so as to monitor a thin-film formation status.

7. The film quality evaluation apparatus according to claim 4, wherein a reflectance at a wavelength of 650 nm or more is used.

8. A production system for a thin-film device comprising: the film quality evaluation apparatus according to claim 7, wherein the light radiation unit is disposed to radiate light from a film surface side on a crystalline silicon film which is formed on a substrate transported in a production line including a thin-film formation process so as to monitor a thin-film formation status.

9. A production system for a thin-film device comprising: the film quality evaluation apparatus according to claim 4, wherein the light radiation unit is disposed to radiate light from a film surface side on a crystalline silicon film which is formed on a substrate transported in a production line including a thin-film formation process so as to monitor a thin-film formation status.

* * * * *